US012133026B2

(12) United States Patent
Caute et al.

(10) Patent No.: US 12,133,026 B2
(45) Date of Patent: Oct. 29, 2024

(54) UNDERWATER CAMERA WITH SONAR FUSION

(71) Applicant: Airmar Technology Corporation, Milford, NH (US)

(72) Inventors: Didier Caute, Lorient (FR); Bruno Marie, Ploemeur (FR); Brice Godreul, Ploemeur (FR)

(73) Assignee: AIRMAR TECHNOLOGY CORPORATION, Milford, NH (US)

( * ) Notice: Subject to any disclaimer, the term of this patent is extended or adjusted under 35 U.S.C. 154(b) by 0 days.

(21) Appl. No.: 17/357,523

(22) Filed: Jun. 24, 2021

(65) Prior Publication Data
US 2021/0409652 A1     Dec. 30, 2021

Related U.S. Application Data

(60) Provisional application No. 63/043,581, filed on Jun. 24, 2020.

(51) Int. Cl.
*H04N 5/225*     (2006.01)
*G01S 7/52*       (2006.01)
(Continued)

(52) U.S. Cl.
CPC ......... *H04N 7/183* (2013.01); *G01S 7/52004* (2013.01); *G01S 15/86* (2020.01);
(Continued)

(58) Field of Classification Search
CPC ............ H04N 5/225; H04N 9/47; H04N 7/18; H04N 7/183; H04N 5/23299; H04N 5/2256; H04N 5/23229; H04N 5/76; H04N 7/002; G01S 15/86; G01S 7/52004; G01S 15/89; G06V 40/10; G06V 20/41; G01N 33/18; H01S 15/96; G06K 9/5289
(Continued)

(56) References Cited

U.S. PATENT DOCUMENTS 4,105,990 A * 8/1978 Rines ................. G01S 15/86
                                                              367/128
6,263,503 B1 * 7/2001 Margulis .......... H04N 21/43637
                                                              348/E5.093
(Continued)

FOREIGN PATENT DOCUMENTS

EP       3650889 A2    5/2020
WO    2021/263028 A1  12/2021

OTHER PUBLICATIONS

Jun, Bong-Huan et al,: "First field-test of 1,4, seabed walking robot CR200", 7-10,13, 2013 Oceans—San Diego, MTS, Sep. 23, 2013 (Sep. 23, 2013), pp. 1-6.
(Continued)

*Primary Examiner* — Daquan Zhao
(74) *Attorney, Agent, or Firm* — Hamilton, Brook, Smith & Reynolds, P.C.

(57) ABSTRACT

A multi-function sensor system comprises a camera and a sonar device to enable various measurements to be achieved in a single unit, or as multiple co-located units, thus reducing the cost of having such multiple functions. The camera and sonar device may be calibrated individually and as a system to provide an accurate and correlated set of optical and acoustic data.

16 Claims, 6 Drawing Sheets

(51) Int. Cl.

| | | |
|---|---|---|
| *G01S 15/86* | (2020.01) | |
| *G01S 15/89* | (2006.01) | |
| *G01S 15/96* | (2006.01) | |
| *G06F 18/25* | (2023.01) | |
| *G06V 20/40* | (2022.01) | |
| *G06V 40/10* | (2022.01) | |
| *H04N 5/76* | (2006.01) | |
| *H04N 7/18* | (2006.01) | |
| *H04N 9/47* | (2006.01) | |
| *H04N 17/00* | (2006.01) | |
| *H04N 23/56* | (2023.01) | |
| *H04N 23/695* | (2023.01) | |
| *H04N 23/80* | (2023.01) | |
| *G01N 33/18* | (2006.01) | |

(52) U.S. Cl.
CPC .............. *G01S 15/89* (2013.01); *G01S 15/96* (2013.01); *G06F 18/251* (2023.01); *G06V 20/41* (2022.01); *G06V 40/10* (2022.01); *H04N 5/76* (2013.01); *H04N 17/002* (2013.01); *H04N 23/56* (2023.01); *H04N 23/695* (2023.01); *H04N 23/80* (2023.01); *G01N 33/18* (2013.01)

(58) Field of Classification Search
USPC .................... 348/169, 61, 94, 107, 142, 135
See application file for complete search history.

(56) References Cited

U.S. PATENT DOCUMENTS

| | | | |
|---|---|---|---|
| 8,638,362 B1* | 1/2014 | Thompson | G01S 15/89 |
| | | | 348/81 |
| 9,197,974 B1* | 11/2015 | Clark | H04R 29/004 |
| 2006/0235635 A1* | 10/2006 | Intrator | G01V 1/28 |
| | | | 702/79 |
| 2012/0130889 A1* | 5/2012 | Lyons | G06Q 20/3272 |
| | | | 705/39 |
| 2017/0023667 A1 | 1/2017 | Laster | |
| 2017/0023676 A1 | 1/2017 | Laster | |
| 2019/0243371 A1 | 8/2019 | Nister et al. | |
| 2021/0329892 A1* | 10/2021 | Kozachenok | G01S 15/96 |
| 2022/0116600 A1* | 4/2022 | Rosewarne | H04N 19/1883 |
| 2022/0301302 A1* | 9/2022 | Murphy | A01K 97/00 |

OTHER PUBLICATIONS

Invitation to Pay Additional Pay Fees and, Where Applicable, Protest Fee for International Application No. PCT/US2021/038961, entitled, "Underwater Camera with Sonar Fusion", mailed Oct. 19, 2021.

Notification of Transmittal of the International Search Report and The Written Opinion of the International Searching Authority for International Application No. PCT/US2021/038961, entitled, "Underwater Camera with Sonar Fusion", mailed Dec. 14, 2021.

PCT International Preliminary Report on Patentability and Written Opinion for International Application No. PCT/US2021/038961, entitled "Underwater Camera with Sonar Fusion," mailed on Jan. 5, 2023.

* cited by examiner

UNDERWATER CAMERA WITH SONAR FUSION

RELATED APPLICATION

This application claims the benefit of U.S. Provisional Application No. 63/043,581, filed on Jun. 24, 2020. The entire teachings of the above application are incorporated herein by reference.

BACKGROUND

Sonar devices and cameras are frequently used to monitor fishing equipment and to track fish. However, sonar devices suffer from limited resolution, while cameras suffer from limited range, especially in a turbid environment.

SUMMARY

The fishing industry lacks existing a combined acousto-optic system that features complementary advantages and functions as a single unit.

In one embodiment, the system includes a camera configured to provide a stream of video data and a sonar device configured to provide a stream of acoustic data representing echoes from an emitted sonar pulse or series of pulses. In some embodiments, the camera and sonar device may be co-located and may be mounted on a rigid frame.

In some embodiments, the system may include a computer processor configured to modify the stream of video data to eliminate distortion introduced by the camera or a component associated therewith. The system may include a non-transitory computer-readable medium for storing the video and acoustic data streams.

In some embodiments, the system may include a computer processor configured to combine the stream of video data with the stream of acoustic data. The system may include a non-transitory computer-readable medium for storing the combined video and acoustic data stream.

In some embodiments, the system may include at least one light source mounted in close proximity to the camera. The system may include a modem configured to transmit the video data stream from the camera to a video display device. The system may include an optical objective and optical dome configured to improve field of view from the camera, establishing a conical region of minimal distortion.

In some embodiments, the camera and sonar device may be mounted to a structure used for fishing or aquaculture. The camera and sonar device may be oriented towards a common target area.

In some embodiments, the system may include one or more mechanical positioners to calibrate the position of the camera and the sonar device.

In some embodiments, the system may include a computer processor configured to perform an analysis on the video and acoustic data streams to determine if one or more physical objects are present. In some embodiments, the system may include at least one sensor used to determine at least one of ambient pressure, ambient temperature, and environmental salinity in a marine environment. The system may include a computer processor configured to perform an analysis on the video and acoustic data streams to determine if one or more fish are present, and to perform further analysis on sensed ambient pressure, ambient temperature, and environmental salinity to determine one or more species of fish present.

In some embodiments, the system may include one or more active pingers configured to transmit a ping signal to the sonar device. The system may include a computer processor configured to determine a distance between the sonar device and a given one of the one or more pingers based on a time delay between the request signal and the response signal.

In another embodiment, a method for performing multiple measurement functions includes receiving, at a camera, a stream of video data, and receiving, at a sonar device, a stream of acoustic data representing echoes from an emitted sonar pulse or series of pulses. The method may include combining, at a computer processor, the stream of video data with the stream of acoustic data. The method may include receiving, from at least one sensor, a measurement of at least one of ambient pressure, ambient temperature, and environmental salinity in a marine environment. The method may include performing an analysis on the video and acoustic data streams to determine if one or more fish are present. The method may include performing an analysis on the measurements of ambient pressure, ambient temperature, and environmental salinity to determine one or more species of fish present.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

The system described below mitigates the need for separate assemblies for performing multiple measurement functions by providing a single assembly that facilitates environmental measurements as well as detection and classification of one or more physical objects. Environmental measurements may include but are not limited to depth, ambient temperature, ambient pressure, and environmental salinity. The system may operate in a medium that may include but is not limited to water or a water-based solution. The water-based solution may include but is not limited to salt water. The salt water medium may include but is not limited to sea water found in a marine environment, brackish water found inland or close to shore, or a controlled solution found in an artificial environment such as a laboratory.

Other embodiments may include separate co-located assemblies that retain the advantages of the single assembly described herein.

Some embodiments are directed to an opto-acoustic measurement system mounted to a structure used for fishing or aquaculture.

Figure 1:
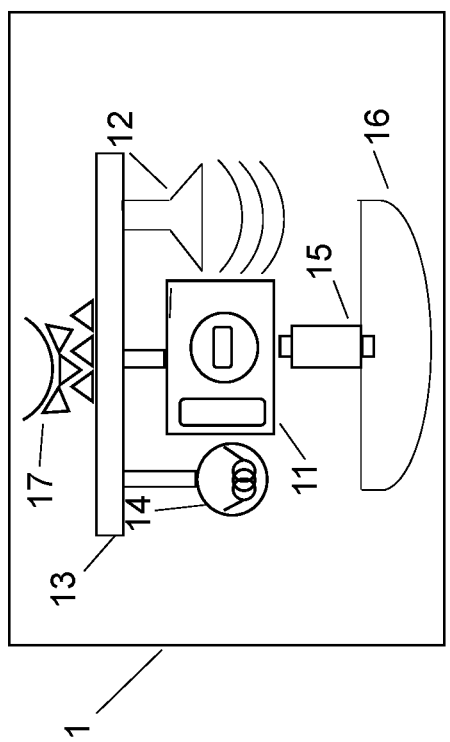
FIG. 1 illustrates co-location and common orientation of camera, sonar device, and optional light source in an opto-acoustic sensor assembly.

Turning now to FIG. 1, a multi-function sensor system is generally denoted by numeral 1 and will hereinafter be referred to as the "system 1." The system 1 comprises a camera 11 that may be mounted to a rigid frame 13. The system 1 further comprises a sonar device 12 that may be mounted to the rigid frame 13. The camera 11 and the sonar device 12 may be mounted in close proximity to each other and may be oriented to sense the same target area. The system 1 may further comprise a light source 14 that may be mounted to the rigid frame 13 in close proximity to the camera 11. The light source 14 may be oriented to illuminate the same target area that the camera 11 is oriented to sense. The system 1 may further comprise an optical objective 15 and, optionally, an optical dome 16 oriented with the camera 11 to establish a 90° field of view from the camera 11. The system 1 may further comprise a mechanical positioner 17 that can be used to adjust the physical position of the rigid frame 13 in three dimensions, resulting in an adjustment to the target area that the camera 11 and the sonar device 12 are oriented to sense. Although not shown in FIG. 1, additional mechanical positioners may be mounted between the camera 11 and the rigid frame 13, and between the sonar device 12 and the rigid frame 13, so that the physical positions of the camera 11 and of the sonar device 12 can be adjusted in three dimensions independently of each other.

Figure 2:
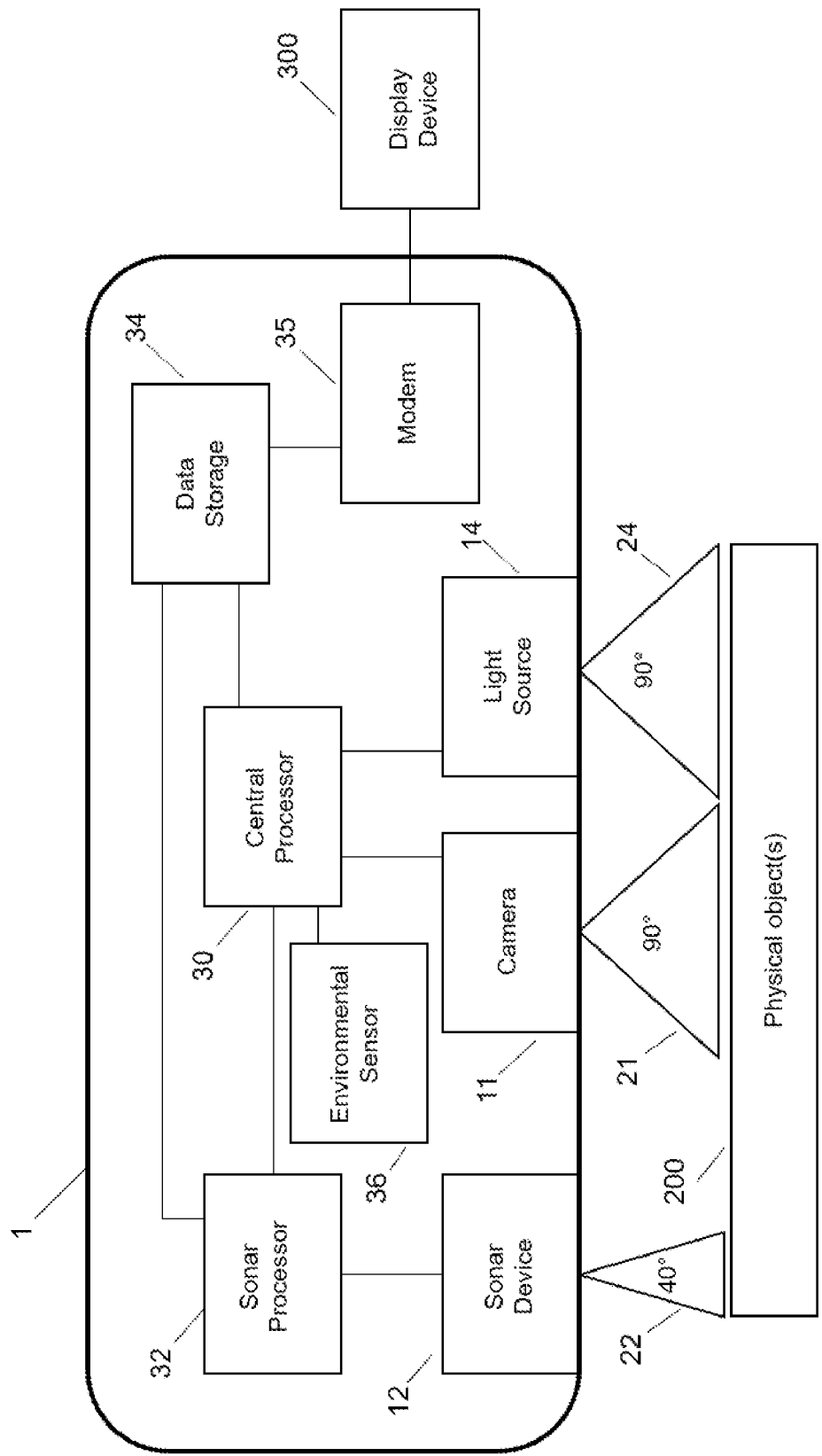
FIG. 2 is a system block diagram of the opto-acoustic sensor assembly as it senses one or more physical objects and presents data to a user through a display device.

FIG. 2 is a schematic block diagram that provides further detail of the system 1. The sonar device 12 is connected to a sonar processor 32. The sonar processor 32 may be embodied in a software-defined platform. The sonar field of view 22 is approximately 40°. The camera field of view 21 is approximately 90°, and the beam of light 24 emitted by the light source 14 illuminates the entire 90° camera field of view 21. FIG. 2 represents the sonar field of view 22, the camera field of view 21, and the beam of light 24 in block format and does not provide any information regarding their relative physical locations. The sonar field of view 22, the camera field of view 21, and the beam of light 24 may be oriented in the same direction towards one or more physical objects 200. It should be understood that the given fields of view are exemplary, and that they can have other values.

An embedded central processor 30 may be connected to the camera 11 and to the sonar processor 32. The central processor 30 may also be connected to the light source 14. A non-transitory computer-readable data storage medium 34 may be connected to the central processor 30 and to the sonar processor 32. A modem 35 may be connected to the data storage medium 34. The modem 35 may be configured to transmit data to an external display device 300. Although not shown in FIG. 2, the modem 35 may also be configured to receive external signals. The external signals may be used to control various elements of the system 1.

Figure 3:
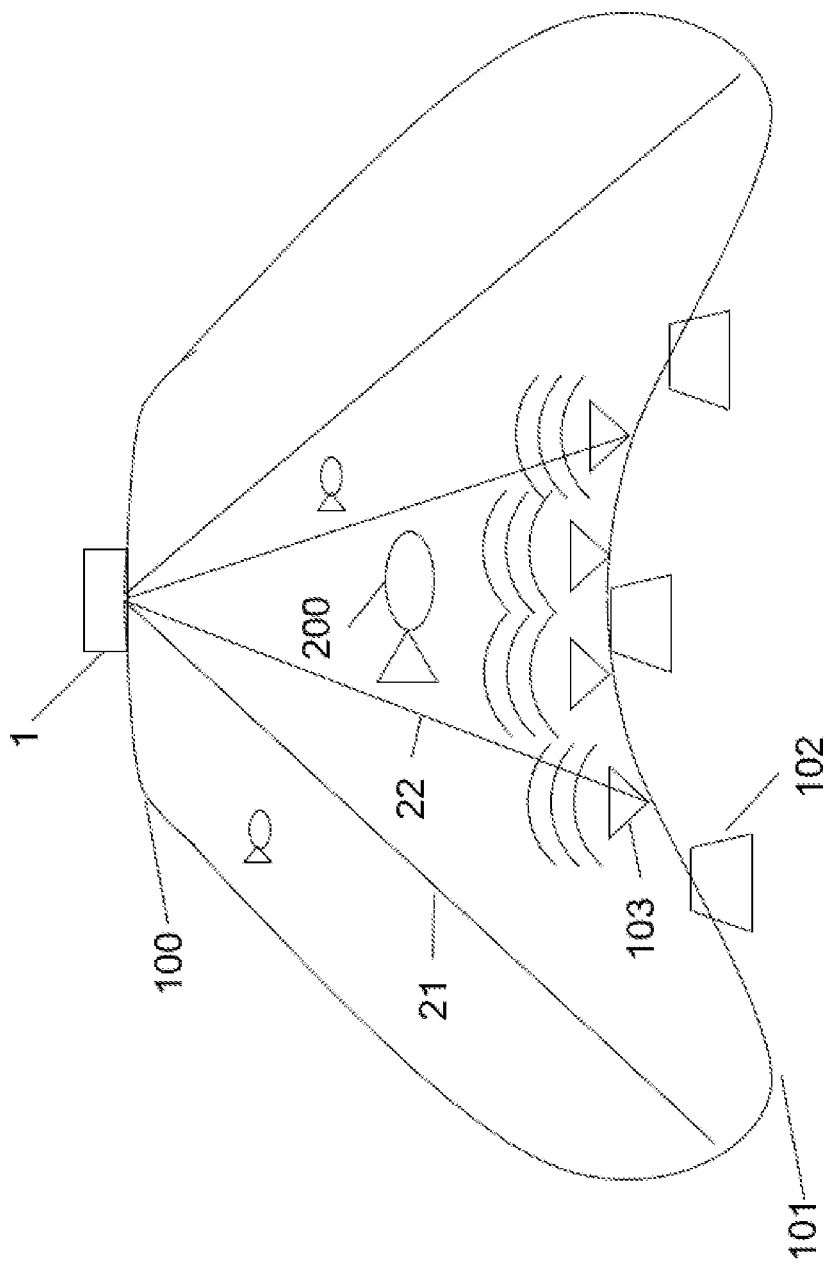
FIG. 3 illustrates placement of the opto-acoustic sensor assembly on a structure used for fishing, according to some embodiments of the present disclosure.

As illustrated in FIG. 3, in an embodiment, the system 1 is mounted to the headrope 100 of a fishing trawl net. The fishing trawl net may be submerged to a depth appropriate for targeting demersal or pelagic fish and may be towed by a vessel, typically a fishing boat. One or more weights 102 may be attached to the footrope 101 of the fishing trawl net. One or more pingers 103 may also be attached to the footrope 101. The one or more pingers 103 may be oriented to transmit sound waves to, and receive sound waves from, the sonar device 12 inside the system 1. The camera field of view 21 and the sonar field of view 22 overlap in order to detect the same one or more physical objects 200. The one or more physical objects 200 may include fish. The one or more physical objects 200 may include the floor of a body of water or one or more features of the floor of the body of water.

In another embodiment, the system 1 may be mounted on a purse seine type net.

In another embodiment, the system 1 may be mounted on a fishing structure meant to remain stationary for a period of time while submerged. The stationary structure may include a crab pot or a lobster pot.

In another embodiment, the system 1 may be mounted on a fish pen structure used in aquaculture.

As can be appreciated, the system 1 includes various hardware components that can be configured to perform various functions using firmware that either resides in the system 1 upon initial programming, or is downloaded at a later time, e.g. to upgrade the system 1 to utilize additional functions.

Figure 4:
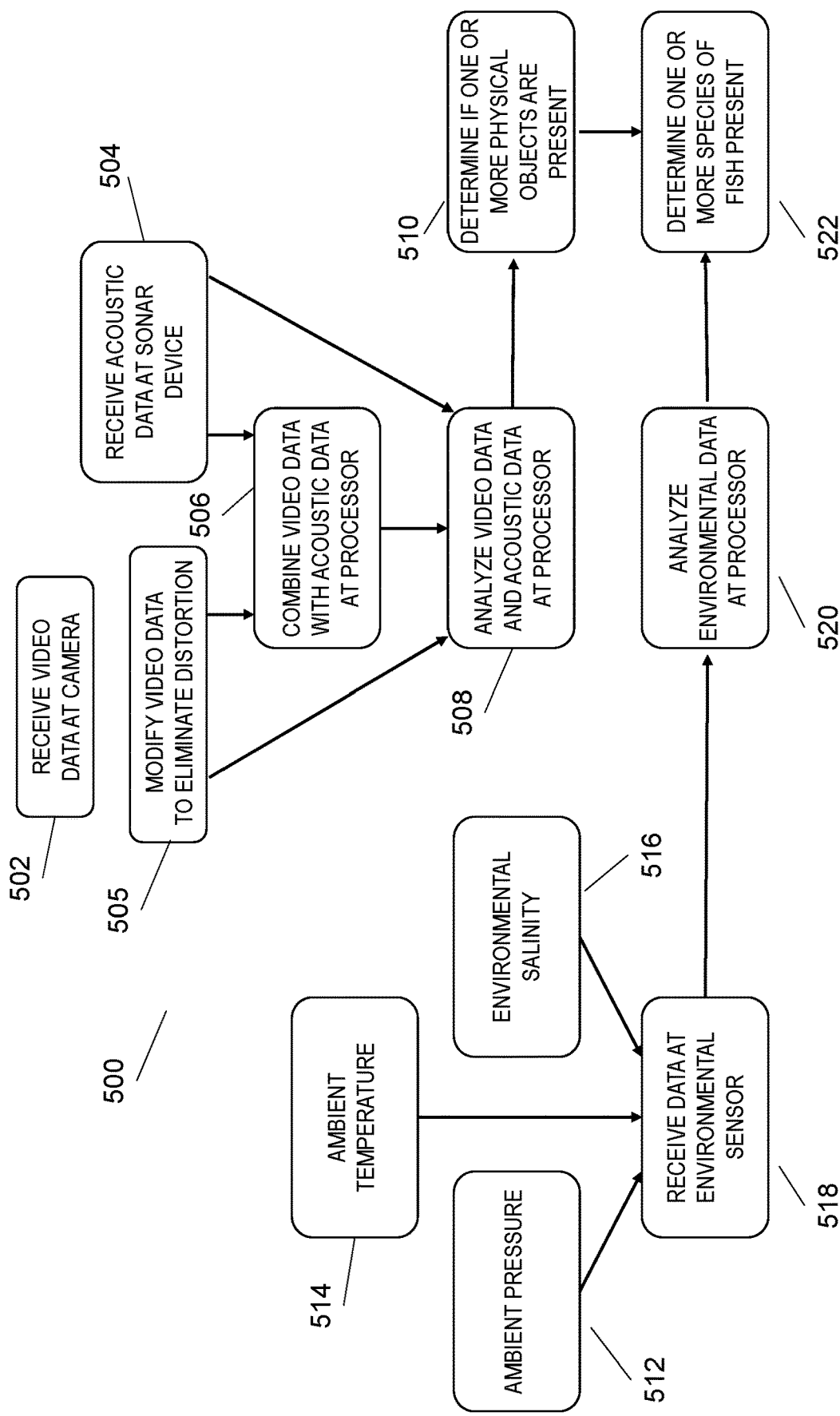
FIG. 4 is a flow diagram, illustrating an example method (or system) according to some embodiments of the present disclosure.

FIG. 4 is a flow diagram illustrating an example method 500 of performing multiple measurement functions, according to some embodiments of the present disclosure. As illustrated in FIG. 4, in some embodiments, the method includes receiving video data 502 at the camera 11. The method includes receiving acoustic data 504 from the sonar device 12. The method may include modifying 505 the stream of video data to eliminate distortion introduced by the camera or a component associated therewith. The method may include combining 506 the video data 502 and acoustic data 504. The method may include performing an analysis 508 on the video data 502 and the acoustic data 504. The method may include performing an analysis 508 on the combined 506 video and acoustic data. The method may include using the analysis 508 to determine 510 if one or more physical objects are present. The method may include receiving environmental data 518 at an environmental sensor 36. The environmental data 518 may include ambient pressure, ambient temperature, and/or environmental salinity. The method may include performing an analysis 520 on the environmental data 518. The method may include using the analysis 520 and the determination 510 if one or more physical objects are present to determine 522 one or more species of fish present.

The sonar device 12 provides low attenuation in a medium comprised of seawater and is not markedly affected by turbidity of the seawater. The sonar device 12 provides long-range detection. The resolution of the sonar device 12 depends on the acoustic wavelength of the transmission and the signal processing employed. In an embodiment, the sonar processor 32 is configured to process 30 beams per second and achieves a detection range of 25 m. In an embodiment, the sonar device 12 uses pulse compression techniques to achieve a depth resolution of approximately 1 cm and a phase resolution of approximately 3 cm. The depth resolution of 1 cm and the phase resolution of 3 cm define a 1 cm×3 cm×3 cm cell that represents a volumetric resolution. The volumetric resolution, over a beam width of 45°, provides a footprint coverage of approximately 4 m in diameter at a range of 5 m from the sonar device 12. It should be understood that these are exemplary values and that other values of beams per second, detection range, depth resolution, phase resolution, volumetric resolution, and footprint coverage may be realized.

The camera 11 provides color information and better resolution than the sonar device 12. However, the camera 11 only enables short-range detection, limited by the turbidity of the medium. In an embodiment, the camera 11 employs a high dynamic range (e.g., 12.3 megapixel, 1 inch×2.3 inch) CMOS sensor. In some embodiments, the camera 11 is capable of recording both individual frames and ultra-fast video. The speed with which the camera 11 captures video may be sufficient to limit the effects of distortion that result from a rolling shutter method of video capture. Rolling shutter is herein defined as a method of image capture wherein a still picture in a still camera or each frame of a video in a video camera is captured not by taking a snapshot of the entire scene at a single instant in time, but rather by scanning across the scene rapidly, either vertically or horizontally. In other words, not all parts of the image of the scene are recorded at exactly the same instant. Though, during playback, the entire image of the scene is displayed at once, as if it represents a single instant in time. This produces predictable distortions of fast-moving objects or rapid flashes of light. This is in contrast with "global shutter" in which the entire frame is captured at the same instant.

In an embodiment, the optical objective 15 may be a wide-angle objective selected and oriented to set the camera field of view 21 to 90° with limited optical distortion to achieve a pixel resolution of 3 mm×2.5 mm. The pixel resolution provides a footprint coverage of approximately 4 m×4 m at a range of 5 m from the camera 11.

In an embodiment, the optical dome 16 provides an interface between the optical objective 15 and the medium that may include water or a water-based solution. The optical dome may reduce refraction at the interface, thus reducing optical distortion in the image received by the camera 11.

In an embodiment, the light source 14 comprises a set of four separate white light sources arranged to create a uniform pattern of light over the 90° camera field of view 21. The light intensity in the periphery of the camera field of view 21 is intentionally greater than the light intensity in the center of the camera field of view 21 to compensate for the increase in light absorption by the medium as the one or more physical objects 200 moves further from nadir. Herein nadir is defined as the direction perpendicular to the plane being imaged by the camera 11.

In an embodiment, the light source comprises a two-dimensional lighting system that produces a narrow beam of light with component wavelengths in the red, green, and blue regions of the visible light spectrum. The beam may rapidly scan the target area to project an image composed of pixels. A digital light processor (DLP) may control the intensity and color of each pixel. The DLP may process multiple image captures to produce a high resolution image file. In this embodiment, the DLP runs faster than the capture rate of the camera 11 to avoid a rolling shutter effect. This embodiment is advantageous in providing uniform lighting regardless of the distance between the camera 11 and the one or more physical objects 200. This embodiment is further advantageous in providing active control of contrast and color for optimal image quality. This embodiment is further advantageous when the one or more physical objects 200 are fish as it provides the capability to adjust the light source either to influence or avoid influencing the behavior of the fish.

In an embodiment, the environmental sensor 36 provides ambient pressure, ambient temperature, and environmental salinity data that may be used to compute the speed of the acoustic waves being transmitted and received by the sonar device 12, improving the accuracy of distance measurements made with the sonar device 12. In another embodiment, a pre-defined speed of sound model may be used for a given medium to refine the accuracy of the distance measurements made with the sonar device 12.

In an embodiment, the modem 35 is a cable modem designed for broadband internet applications. The cable modem may be connected to a vessel such as a fishing boat via a coaxial cable. The cable modem may be connected to the computer-readable data storage medium 24 via an ethernet cable.

In some embodiments, the camera 11 is powered by one or more batteries internal to the camera 11.

In some embodiments, the acoustic waves emitted by the sonar device 12 are fully synchronized with the rate of image capture of the camera 11. In an embodiment, the sonar device 12 pings 30 times per second, and the camera captures 30 frames per second, providing a 25 m range. In another embodiment, the sonar device 12 pings 10 times per second, while the camera 11 captures 30 frames per second, providing a 75 m range and an improvement in data quality over an embodiment wherein the camera 11 would capture only 10 frames per second.

In an embodiment, the embedded central processor 30 uses both video data from the camera 11 and acoustic data from the sonar device 12 to determine one or more species of fish present and to determine the size of the fish present. The central processor 30 can be configured to correlate acoustic echoes from the fish to determine a three-dimensional location of the fish relative to the system 1, a target strength of the fish, and a direction of travel of the fish. The central processor 30 can further be configured to correlate sonar data with video data to provide a more precise estimate of fish size. The central processor 30 can further be configured to correlate sonar and video data with environmental data from the environmental sensor 36 and with historical environmental data to provide an improved method for fish species identification.

In some embodiments, the sonar device 12 and camera 11, mounted on the rigid frame 13, are individually calibrated to achieve a targeted resolution and accuracy, followed by a final calibration of the complete system 1. In some embodiments, a black and white checkerboard pattern is placed at the bottom of an acoustic test tank containing water. Buoyant balls may be attached above known corners of the checkerboard pattern at different known heights above the bottom. The rigid frame 13, with the camera 11 and the sonar device 12 attached to the rigid frame 13, may be submerged in the tank at a depth several meters above the bottom. The video data from the camera 11 and the acoustic data from the sonar device 12 may be analyzed by the central processor 30 to create a rotational matrix and vector map that may be used to align the optical and acoustic images in three-dimensional space.

In some embodiments, one or more active pingers 103 are configured to transmit a ping signal to the sonar device 12. The ping signal may be correlated with precisely known time delays by the sonar processor 32 to measure distance to known points of interest with fine (e.g., centimeter) resolution. In an embodiment, this distance information, combined with very accurate bottom detection achieved by the sonar, enables the system 1 to determine the impact of the footrope 101 of a fishing trawl net on the bottom. Limiting this impact reduces the energy required from the vessel to tow the trawl net and also reduces wear and tear on the trawl gear. In some embodiments, chains are attached to the footrope 101 to ensure that the footrope 101 makes contact with the bottom. Based on data describing the impact of the footrope 101 on the bottom, a number of chains may be removed or added to ensure bottom contact while minimizing the extent to which the bottom is disturbed. This is advantageous because superfluous disruption of the bottom can cause sediment from the bottom to become entrained in the water, increasing the turbidity of the water and degrading the quality of the image produced by the camera 11.

Figure 5:
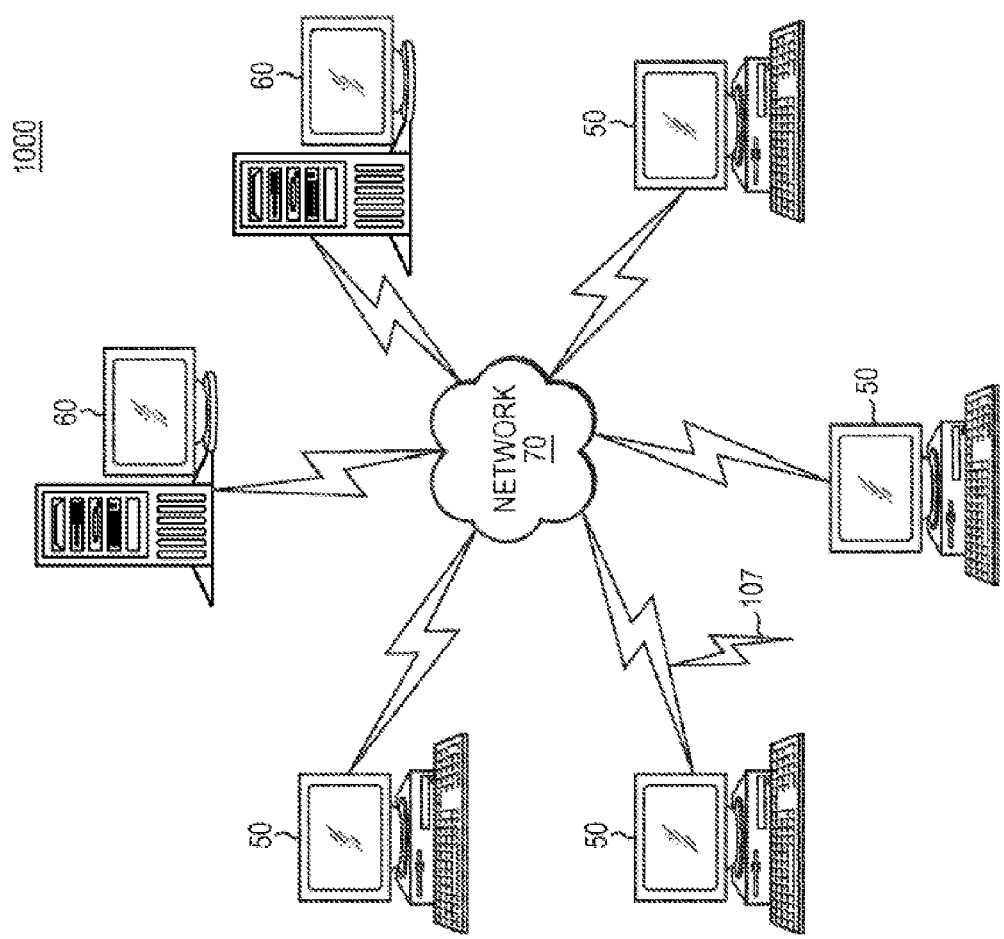
FIG. 5 illustrates a computer network (or apparatus, or system) or similar digital processing environment, according to some embodiments of the present disclosure.

FIG. 5 illustrates a computer network (or system) 1000 or similar digital processing environment, according to some embodiments of the present disclosure. Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Client computers/devices 50 may be configured with a computing module (located at one or more of elements 50, 60, and/or 70). In some embodiments, a user may access the computing module executing on the server computers 60 from a user device, such a mobile device, a personal computer, or any computing device known to one skilled in the art without limitation. According to some embodiments, the client devices 50 and server computers 60 may be distributed across a computing module.

Server computers 60 may be configured as the computing modules which communicate with client devices 50 for providing access to (and/or accessing) databases that include data associated with target objects and/or reference objects. The server computers 60 may not be separate server computers but part of cloud network 70. In some embodiments, the server computer (e.g., computing module) may enable users to determine location, size, or number of physical objects (including but not limited to target objects and/or reference objects) by allowing access to data located on the client 50, server 60, or network 70 (e.g., global computer network). The client (configuration module) 50 may communicate data representing the physical objects back to and/or from the server (computing module) 60. In some embodiments, the client 50 may include client applications or components executing on the client 50 for determining location, size, or number of physical objects, and the client 50 may communicate corresponding data to the server (e.g., computing module) 60.

Some embodiments of the system 1000 may include a computer system for determining location, size, or number of physical objects. The system 1000 may include a plurality of processors 84. The system 1000 may also include a memory 90. The memory 90 may include: (i) computer code instructions stored thereon; and/or (ii) data representing location, size, or number of physical objects. The data may include segments including portions of the location, size, or number of physical objects. The memory 90 may be operatively coupled to the plurality of processors 84 such that, when executed by the plurality of processors 84, the computer code instructions may cause the computer system 1000 to implement a computing module (the computing module being located on, in, or implemented by any of elements 50, 60, 70 of FIG. 5 or elements 82, 84, 86, 90, 92, 94, 95 of FIG. 6) configured to perform one or more functions.

Figure 6:
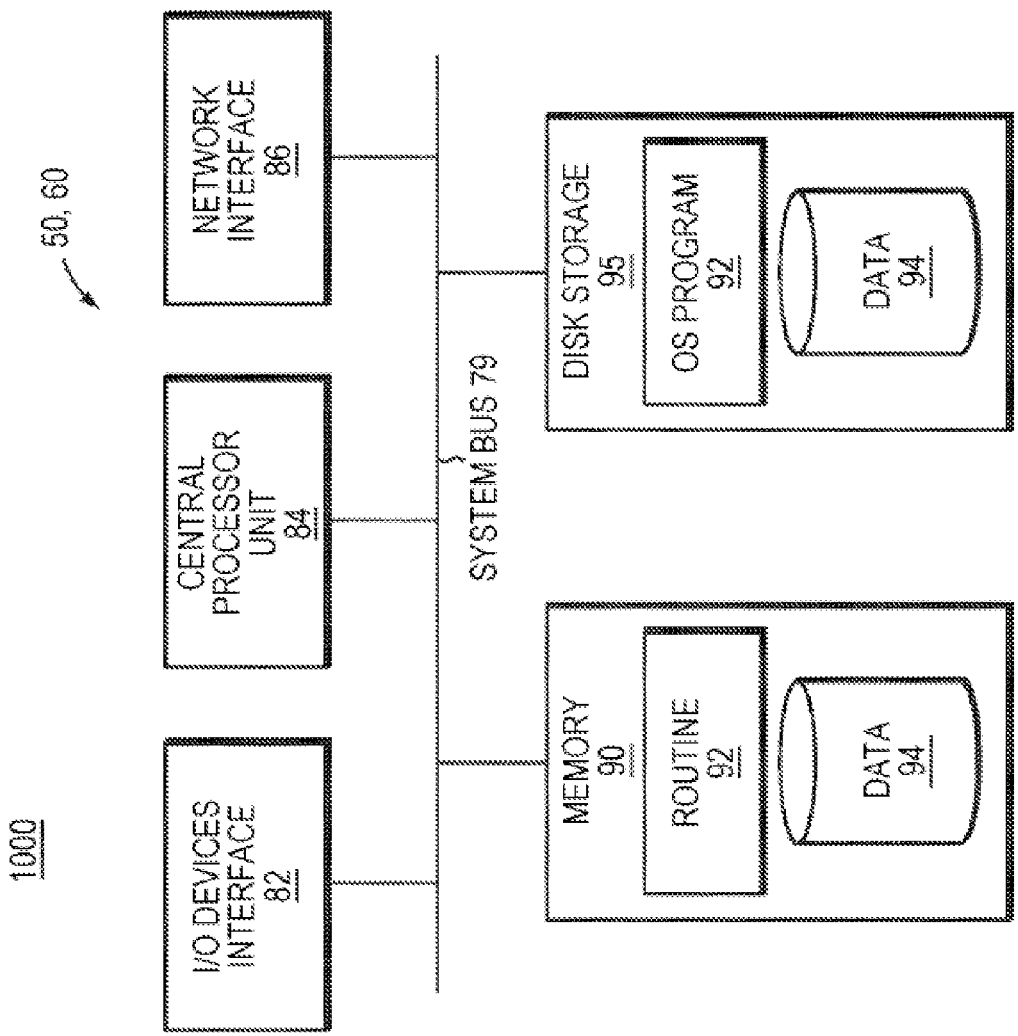
FIG. 6 illustrates a diagram of an example internal structure of a computer (e.g., client processor/device or server computers) in the computer system (and apparatus) of FIG. 5, according to some embodiments of the present disclosure.

According to some embodiments, FIG. 6 is a diagram of an example internal structure of a computer (e.g., client processor/device 50 or server computers 60) in the computer system 1000 of FIG. 5. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 5). Memory 90 provides volatile storage for computer software instructions 92 and data 94 used to implement some embodiments (e.g., video data stream and sonar data stream described herein). Disk storage 95 provides non-volatile storage for computer software instructions 92 and data 94 used to implement an embodiment of the present disclosure. A central processor unit 84 is also attached to the system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the present disclosure. The computer program product 92 can be installed by any suitable software installation procedure, as is well known in the art. In another embodiment, at least a portion of the software instructions may also be downloaded over a cable, communication and/or wireless connection. Other embodiments may include a computer program propagated signal product 107 (of FIG. 6) embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the routines/program 92 of the present disclosure.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Embodiments or aspects thereof may be implemented in the form of hardware (including but not limited to hardware circuitry), firmware, or software. If implemented in software, the software may be stored on any non-transient computer readable medium that is configured to enable a processor to load the software or subsets of instructions thereof. The processor then executes the instructions and is configured to operate or cause an apparatus to operate in a manner as described herein.

Further, hardware, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etc.

It should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and, thus, the data processors described herein are intended for purposes of illustration only and not as a limitation of the embodiments.

While example embodiments have been particularly shown and described, it will be understood by those skilled in the art that various changes in form and details may be made therein without departing from the scope of the embodiments encompassed by the appended claims.

What is claimed is:

1. A system for performing multiple functions comprising:
   a camera including an image sensor and configured to provide a stream of video data representing a scene in a camera field of view of the camera, the scene sensed via the image sensor based on a rate of image capture of the camera;
   the camera operatively coupled to a sonar device with a sonar field of view, the sonar field of view configured to overlap with the camera field of view, the sonar device configured to provide a stream of acoustic data representing echoes from an emitted sonar pulse or series of pulses, the emitted sonar pulse or series of pulses from the sonar device synchronized with the rate of image capture of the camera; and
   a computer processor configured to combine the stream of video data with the stream of acoustic data to perform an analysis on the stream of video data representing the scene sensed via the image sensor and the stream of acoustic data representing the echoes to determine if one or more physical objects are present.

2. The system of claim 1, further comprising a non-transitory computer-readable medium for storing the video and acoustic data streams.

3. The system of claim 1, wherein the computer processor is further configured to modify the stream of video data to eliminate distortion introduced by the camera or a component associated therewith.

4. The system of claim 1, further comprising a non-transitory computer-readable medium for storing the combined video and acoustic data stream.

5. The system of claim 1, further comprising at least one light source mounted in close proximity to the camera.

6. The system of claim 1, further comprising a modem configured to transmit the video data stream from the camera to a video display device.

7. The system of claim 1, wherein the camera and sonar device are co-located and mounted on a rigid frame.

8. The system of claim 1, wherein the camera and sonar device are mounted to a structure used for fishing or aquaculture.

9. The system of claim 1, wherein the camera and sonar device are oriented towards a common target area.

10. The system of claim 1, further comprising one or more mechanical positioners to calibrate the position of the camera and sonar device.

11. The system of claim 1, further comprising at least one sensor used to determine at least one of ambient pressure, ambient temperature, and environmental salinity in a marine environment.

12. The system of claim 11, wherein the computer processor is further configured to perform an analysis on the video and acoustic data streams to determine if one or more fish are present, and to perform further analysis on sensed ambient pressure, ambient temperature, and environmental salinity to determine one or more species of fish present.

13. The system of claim 1, further comprising:
   one or more active pingers configured to transmit a ping signal to the sonar device; and
   wherein the computer processor is further configured to determine a distance between the sonar device and a given one of the one or more pingers based on a time delay between a request signal and a response signal.

14. A method for performing multiple measurement functions comprising:
   providing, by a camera including an image sensor, a stream of video data representing a scene in a camera field of view of the camera, the scene sensed via the image sensor based on a rate of image capture of the camera;
   providing, by a sonar device with a sonar field of view, a stream of acoustic data representing echoes from an emitted sonar pulse or series of pulses, the sonar field of view overlapping the camera field of view, the emitted sonar pulse or series of pulses from the sonar device synchronized with the rate of image capture of the camera; and
   at a computer processor, combining the stream of video data with the stream of acoustic data and performing an analysis on the stream of video data representing the scene sensed via the image sensor and the stream of acoustic data representing the echoes to determine if one or more physical objects are present.

15. The method of claim 14 further comprising, at a computer processor, modifying the stream of video data to eliminate distortion introduced by the camera or a component associated therewith.

16. The method of claim 14 further comprising:
   receiving, from at least one sensor, a measurement of at least one of ambient pressure, ambient temperature, and environmental salinity in a marine environment; and
   performing an analysis on:
   the video and acoustic data streams to determine if one or more fish are present; and
   the measurements of ambient pressure, ambient temperature, and environmental salinity to determine one or more species of fish present.

* * * * *